(12) United States Patent
Freeman et al.

(10) Patent No.: US 9,242,114 B2
(45) Date of Patent: Jan. 26, 2016

(54) RESCUER PROTECTION FROM ELECTRICAL SHOCK DURING DEFIBRILLATION

(71) Applicant: ZOLL Medical Corporation, Chelmsford, MA (US)

(72) Inventors: Gary A. Freeman, Newton Center, MA (US); Weilun Quan, Dracut, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 56 days.

(21) Appl. No.: 14/091,455

(22) Filed: Nov. 27, 2013

(65) Prior Publication Data

US 2015/0148856 A1     May 28, 2015

(51) Int. Cl.
| | |
|---|---|
| *A61N 1/39* | (2006.01) |
| *A61B 5/0452* | (2006.01) |
| *A61B 5/00* | (2006.01) |
| *A61H 31/00* | (2006.01) |

(52) U.S. Cl.
CPC ............ *A61N 1/3987* (2013.01); *A61B 5/0452* (2013.01); *A61B 5/4836* (2013.01); *A61N 1/3931* (2013.01); *A61H 31/005* (2013.01); *A61H 2201/5058* (2013.01)

(58) Field of Classification Search
CPC . A61N 1/3925; A61N 1/3987; A61N 1/3968; A61N 1/39
USPC ........................................................ 607/5, 6
See application file for complete search history.

(56) References Cited

U.S. PATENT DOCUMENTS

| | | | |
|---|---|---|---|
| 2010/0022904 A1* | 1/2010 | Centen | ........................ 600/534 |
| 2012/0259156 A1* | 10/2012 | Freeman | ........................ 600/14 |

* cited by examiner

*Primary Examiner* — Amanda Patton
*Assistant Examiner* — Philip Edwards
(74) *Attorney, Agent, or Firm* — Fish & Richardson P.C.

(57) ABSTRACT

This document relates to cardiac resuscitation, and in particular to systems and techniques for protecting rescuers from electrical shock during defibrillation of a patient.

37 Claims, 8 Drawing Sheets

RESCUER PROTECTION FROM ELECTRICAL SHOCK DURING DEFIBRILLATION

TECHNICAL FIELD

This document relates to cardiac resuscitation, and in particular to systems and techniques for protecting rescuers from electrical shock during defibrillation of a patient.

BACKGROUND

CPR is a process by which one or more rescuers may provide chest compressions and ventilation to a victim/patient who has suffered an adverse cardiac event—by popular terms, a heart attack. Chest compressions are considered to be the most important element of CPR during the first five to eight minutes after CPR efforts begin, because chest compressions help maintain circulation through the body and in the heart itself, which is the organ that can sustain the most damage from an adverse cardiac event. CPR may be performed by a team of one or more rescuers, particularly when the rescuers are professionals, such as emergency medical technicians (EMTs) on an ambulance crew. One rescuer can provide the chest compressions and another can time the ventilations of the patient to match the chest compressions according to appropriate CPR protocol. The CPR can be performed in conjunction with providing shocks to the patient with an external defibrillator, such as from an automatic external defibrillator (AED) that is designed to be used by laypeople. Such AEDs often provide audible information to rescuers, such as "push harder" (when the rescuer is not performing chest compressions forcefully enough), "stop CPR," "stand back" (because a shock is about to be delivered), and the like.

SUMMARY

This document describes systems and techniques that help protect rescuers from harmful electrical shock during defibrillation of a patient. For example, during CPR, the defibrillator (or another computing device) can monitor a physiologic signal of the rescuer such as an ECG, SpO2, or heartbeat signal and synchronize delivery of the defibrillation shock to the patient with the physiologic signal of the rescuer to avoid vulnerable periods of the rescuer's heart cycle, such as the time period surrounding the T wave. For example, during hands-on CPR, the defibrillator (or another computing device) can monitor an ECG signal of the rescuer and synchronize delivery of the defibrillation shock to the patient with the ECG signal of the rescuer to avoid vulnerable periods of the rescuer's heart cycle, such as the time period surrounding the T wave. In another example, the defibrillator can monitor electrical contact between the rescuer and the patient based on a small signal applied to ECG pads on the patient and then prohibit and/or discontinue delivery of a defibrillation shock if electrical contact between the rescuer and patient is detected.

In some aspects, a system includes a first set of ECG leads configured to be placed in contact with the skin of a rescuer, a second set of ECG leads configured to be placed in contact with the skin of a patient; and a computing device connected to the first and second set of ECG leads. The computing device is configured to determine whether a defibrillating shock to the patient's heart is suitable therapy based on one or more electrocardiogram signals of the patient received from the second set of ECG leads and determine a gating signal configured to prohibit administration of the defibrillating shock to the patient's heart during one or more portions of the cardiac cycle of the rescuer, the gating signal determined based on one or more electrocardiogram signals of the rescuer received from the first set of ECG leads.

Embodiments can include one or more of the following.

The configurations to determine the gating signal can include configurations to determine the gating signal such that the gating signal prohibits administration of the defibrillating shock to the patient's heart during a time period surrounding a T wave in the ECG of the rescuer.

The configurations to determine the gating signal can include configurations to determine the gating signal such that the gating signal prohibits administration of the defibrillating shock to the patient's heart during one or more vulnerable periods of the cardiac cycle of the rescuer.

The configurations to determine the gating signal can include configurations to receive the electrocardiogram signal of the rescuer from the first set of ECG leads, determine a location of an R wave in the ECG signal of the rescuer, determine a location of a T wave in the ECG signal of the rescuer, and determine a time period measured from the R wave during which administration of the defibrillating shock to the patient's heart is prohibited, the time period including at least a portion of the T wave.

The configurations to determine the gating signal can include configurations to receive the electrocardiogram signal of the rescuer from the first set of ECG leads, determine a location of the T wave in the ECG signal of the rescuer, and determine a time period that includes at least a portion of the T wave during which administration of the defibrillating shock to the patient's heart is prohibited.

The one or more portions of the cardiac cycle of the rescuer can include at least an interval from about 20% of the peak T wave voltage on the rising edge of the T wave to about 20% of the peak T wave voltage on the falling edge of the T wave.

The one or more portions of the cardiac cycle of the rescuer can include the entire duration of the T wave.

The one or more portions of the cardiac cycle can include the relative refractory period.

The one or more portions of the cardiac cycle of the rescuer consist essentially of an interval from about 20% of the peak T wave voltage on the rising edge of the T wave to about 20% of the peak T wave voltage on the falling edge of the T wave.

The one or more portions of the cardiac cycle of the rescuer consist essentially of the entire duration of the T wave.

The one or more portions of the cardiac cycle consist essentially of the relative refractory period.

The system can also include a third set of ECG leads configured to be placed in contact with the skin of a second rescuer.

The configurations to determine the gating signal can include configurations to determine the gating signal based on electrocardiogram signals from the first and third ECG leads to prohibit administration of the defibrillating shock to the patient's heart during one or more vulnerable periods.

In some additional aspects, a medical system can include a device configured to be placed in contact with the skin of a rescuer, an ECG lead configured to be placed in contact with the skin of the patient, and a safety mechanism configured to detect electrical contact between the patient and the rescuer by applying a signal to the ECG lead and measuring a signal responsive to the applied signal at the device in contact with the skin of the rescuer and prohibit delivery of a defibrillation shock upon detection of electrical contact between the rescuer and patient.

Embodiments can include one or more of the following.

The safety mechanism can be further configured to enable delivery of the defibrillating shock to the patient upon detection of the absence of contact between the patient and the rescuer.

Measuring the signal responsive to the applied signal can include measuring a signal transmitted between the ECG lead and the device in contact with the skin of the rescuer using the patient's body and the rescuer's body as conductive mediums.

The device configured to be placed in contact with the skin of the rescuer can include a wrist strap.

In some aspects, a method includes receiving a first ECG signal from a first set of ECG leads in contact with the skin of a rescuer, receiving a second ECG signal from a second set of ECG leads in contact with the skin of a patient, determining whether a defibrillating shock to the patient's heart is suitable therapy based on one or more electrocardiogram signals of the patient received from the second set of ECG leads, and determining a gating signal configured to prohibit administration of the defibrillating shock to the patient's heart during one or more portions of the cardiac cycle of the rescuer, the gating signal determined based on one or more electrocardiogram signals of the rescuer received from the first set of ECG leads.

Embodiments can include one or more of the following.

Determining the gating signal can include determining the gating signal such that the gating signal prohibits administration of the defibrillating shock to the patient's heart during a time period surrounding a T wave in the ECG of the rescuer.

Determining the gating signal can include determining the gating signal such that the gating signal prohibits administration of the defibrillating shock to the patient's heart during one or more vulnerable periods of the cardiac cycle of the rescuer.

Determining the gating signal can include receiving the electrocardiogram signal of the rescuer from the first set of ECG leads, determining a location of an R wave in the ECG signal of the rescuer, determining a location of a T wave in the ECG signal of the rescuer, and determining a time period measured from the R wave during which administration of the defibrillating shock to the patient's heart is prohibited, the time period including at least a portion of the T wave.

Determining the gating signal can include receiving the electrocardiogram signal of the rescuer from the first set of ECG leads, determining a location of the T wave in the ECG signal of the rescuer, and determining a time period that includes at least a portion of the T wave during which administration of the defibrillating shock to the patient's heart is prohibited.

The one or more portions of the cardiac cycle of the rescuer can include at least an interval from about 20% of the peak T wave voltage on the rising edge of the T wave to about 20% of the peak T wave voltage on the falling edge of the T wave.

The one or more portions of the cardiac cycle of the rescuer can include the entire duration of the T wave.

The one or more portions of the cardiac cycle can include the relative refractory period.

In some additional aspects, a method can include applying a signal to an ECG lead in contact with the skin of the patient, measuring a signal at a device in contact with the skin of a rescuer, the signal being responsive to the applied signal, detecting electrical contact between the patient and the rescuer based on the detected signal, and prohibiting delivery of a defibrillation shock upon detection of electrical contact between the rescuer and patient.

The method can also include enabling delivery of the defibrillating shock to the patient upon detection of the absence of contact between the patient and the rescuer.

Measuring the signal responsive to the applied signal can include measuring a signal transmitted between the ECG lead and the device in contact with the skin of the rescuer using the patient's body and the rescuer's body as conductive mediums.

In some additional aspects, a system includes a sensor placed in contact with the skin of a rescuer, a set of ECG leads configured to be placed in contact with the skin of a patient, and a computing device connected to the sensor and the ECG leads. The computing device is configured to determine whether a defibrillating shock to the patient's heart is suitable therapy based on one or more electrocardiogram signals of the patient received from the second set of ECG leads and determine a gating signal configured to prohibit administration of the defibrillating shock to the patient's heart during one or more portions of the cardiac cycle of the rescuer, the gating signal determined based on one or more physiologic signals of the rescuer received from the sensor.

Embodiments can include one or more of the following.

The sensor can be an SpO2 sensor.

The configurations to determine the gating signal can include configurations to determine the gating signal such that the gating signal prohibits administration of the defibrillating shock to the patient's heart during a time period surrounding a T wave in the patient's cardiac cycle based on the SpO2 signal of the rescuer.

The configurations to determine the gating signal can include configurations to determine the gating signal such that the gating signal prohibits administration of the defibrillating shock to the patient's heart during one or more vulnerable periods of the cardiac cycle of the rescuer.

The configurations to determine the gating signal can include configurations to receive an SpO2 signal from the sensor, determine a location of a peak in the SpO2 signal of the rescuer, determine a location in the SpO2 signal of the rescuer corresponding to a location of a T wave in the patient's cardiac cycle, and determine a time period measured from the peak in the SpO2 signal during which administration of the defibrillating shock to the patient's heart is prohibited, the time period including at least a portion of the T wave.

The techniques described here can have one or more of the following advantages. Gating delivery of a defibrillation shock to a patient based on the ECG signal(s) of the rescuer(s) to avoid vulnerable periods in the heart cycles of the rescuer(s) can help to provide protection to rescuer(s) from electrical shock. In another example, discontinuing delivery of a defibrillation shock during administration (e.g., after a portion of the deliberation shock has already been delivered and a portion of the electrical shock remains to be delivered) based on a determination that the rescuer has re-initiated contact with the patient can provide the advantage of protecting the rescuer from electrical shock.

Other features and advantages will be apparent from the description and drawings, and from the claims.

DETAILED DESCRIPTION

This description discusses systems and techniques for guiding the provision of care to a patient, such as the provision of CPR and delivery of defibrillating energy (a shock) to a victim of cardiac arrest in a manner that protects the rescuer from harmful effects of the defibrillation shock. For example, a portable electronic can include common features for both delivering defibrillating energy (a shock) to a victim of cardiac arrest through electrodes placed on the torso of the patient and also protecting the rescuer from electrical shock during defibrillation.

In some examples, the defibrillator can receive ECG signal(s) for one or more rescuers providing treatment to the patient and use the ECG signal(s) to gate or time the delivery of the defibrillating energy. For example, the ECG of the rescuer can be monitored to determine regions of electrical activity of the rescuer's heart that are vulnerable and the system can prohibit administering an electrical shock during those periods. Exemplary periods can include the periods surrounding the T wave portion in the rescuer's ECG signal.

In another example, the defibrillator may also be provided with a safety mechanism for protecting rescuers from electrical shock during the delivery of the defibrillating energy. In one particular example, a mechanism is provided to disable delivery of electrical shock when the rescuer's hands (or other body parts) are in contact with the patient.

Figure 1:
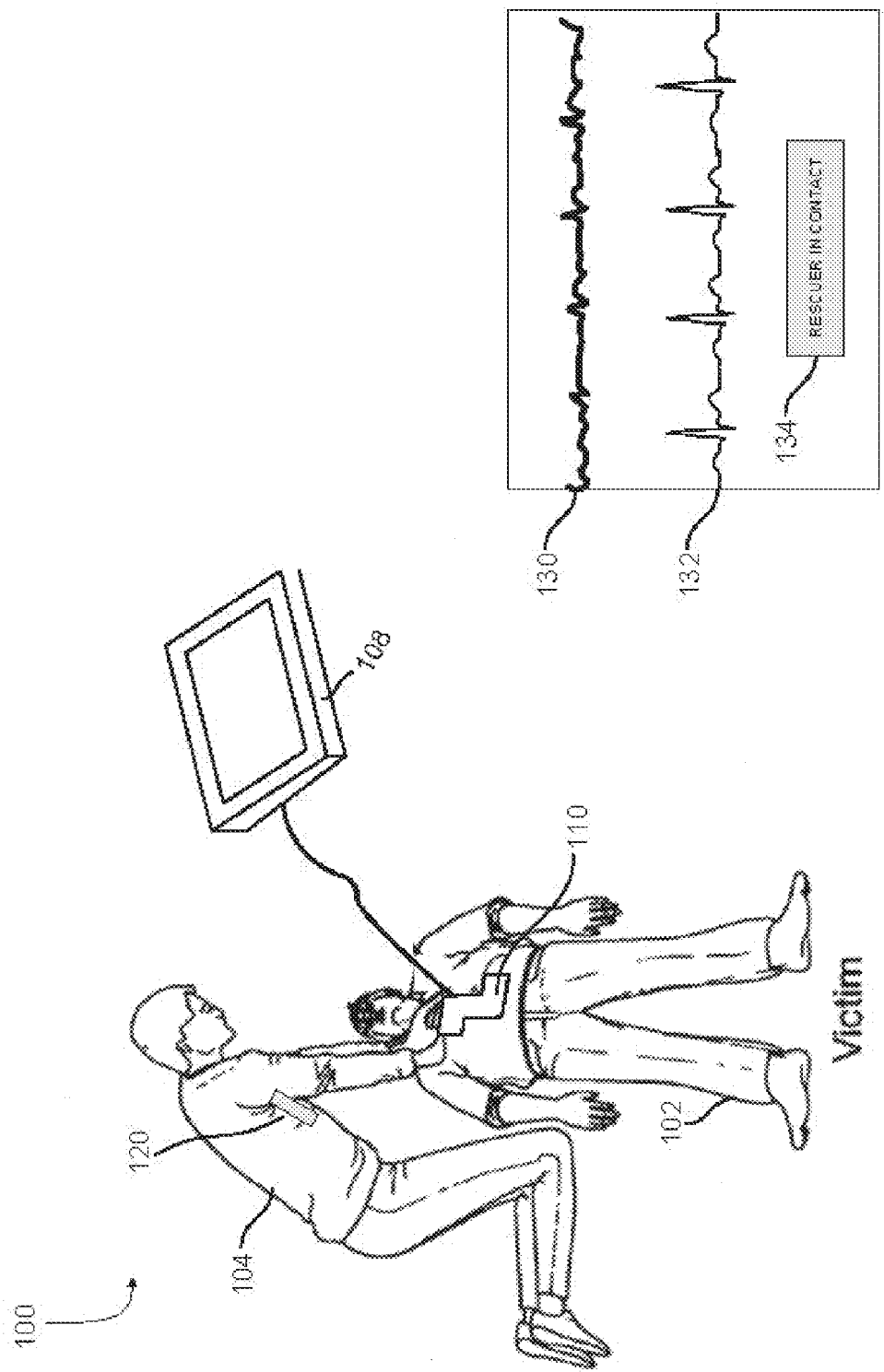
FIG. 1A is an overhead view of a rescuer performing CPR on a patient.
FIG. 1B shows ECG signals for the patient and rescuer.

FIG. 1A is an overhead view of a rescuer 104 performing CPR on a patient 102 at a rescue scene 100 using an electronic system that instructs the rescuer in his/her performance of the CPR. The rescue scene 100 can be a scene at which the patient is undergoing a resuscitation event, such as a patient undergoing cardiac arrest, ventilatory arrest, or trauma (e.g., from an injury such as a gunshot wound or a fall). In this example, rescuer 104 is already in position and providing care to the patient 102. The rescuer 104 may be a lay rescuer who was in the vicinity of the patient 102 when the patient 102 required care, or may be trained medical personnel, such as emergency medical technicians (EMTs). Although a single rescuer is shown here for purposes of explanation, additional rescuers may also care for the patient 102, and may be included in a rotation of rescuers providing particular components of care to the patient 102 (e.g., chest compressions, ventilation, administration of drugs, and other provisions of care).

An electrode assembly 110 is shown in a normal position on the patient 102. In this example, the electrode assembly 110 is an assembly that combines an electrode positioned high on the right side of the patient's torso and an electrode positioned low on the left side of the patient's torso, along with a sensor package located over the patient's sternum. The sensor package may include an accelerometer or similar sensor package that may be used in cooperation with a computer located in the defibrillator 108 to help guide the administration of CPR.

A separate electrode assembly 120 is shown in position on the rescuer 104. In this example, the electrode assembly 120 is an assembly that includes ECG leads to monitor the heart cycle of the rescuer.

The defibrillator 108 in this example is connected to both the electrode assembly 110 and electrode assembly 120. Thus, the defibrillator 108 can obtain and analyze ECG signals from both the patient 102 and the rescuer 104 (e.g., signals 130 and 132 in FIG. 1B, respectively). As described in more detail herein, the ECG signals 130 and 132 for the patient and the rescuer are used to determine when delivery of a defibrillation shock could be beneficial and when to prohibit/allow the defibrillation shock based on the heart cycle of the rescuer. Thus, by monitoring the ECG of the rescuer 104, the defibrillator 108 can identify regions of electrical activity of the rescuer's heart that are vulnerable to electrical shock and prohibit delivery of the defibrillation shock (via electrode assembly 110) to the patient during those periods. The defibrillator 108 may take a generally common form, and may be a professional style defibrillator (such as the R-SERIES, M-SERIES, or E-SERIES from ZOLL Medical Corporation of Chelmsford, Mass., or an automated external defibrillator (AED), including the AED PLUS, or AED PRO from ZOLL Medical Corporation).

Figure 2:
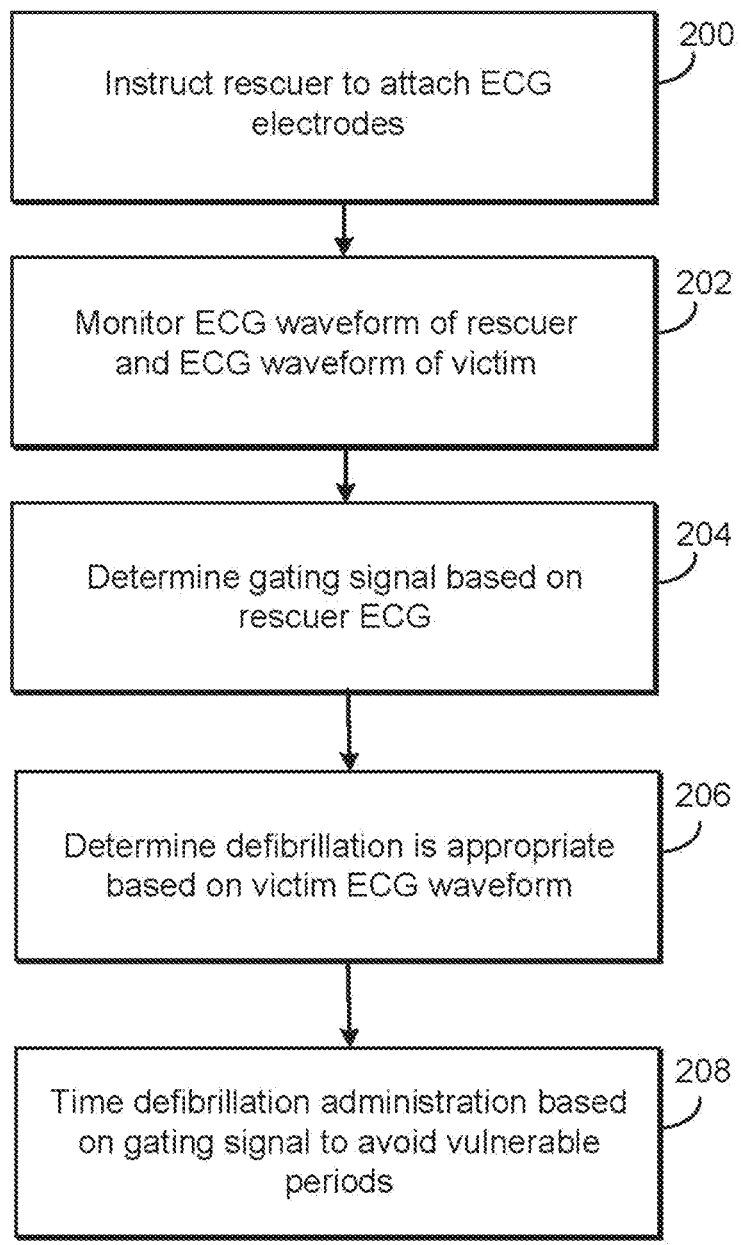
FIG. 2 is a flowchart of a process for timing defibrillation administration based on a gating signal.

FIG. 2 shows a flowchart of a process for timing defibrillation shock administration based on a gating signal to avoid administration during vulnerable periods in a rescuer's heart cycle. In order to monitor the heart rhythms of both the patient and the rescuer, the defibrillator instructs the rescuer to attach ECG electrodes to both him/herself and to the patient (200). After the electrodes have been attached, the defibrillator receives and monitors the ECG waveform of the rescuer and the ECG waveform of the patient (202). For example, the ECG electrodes for both the rescuer and the patient can be connected by wired or wireless connections to the defibrillator. If a wireless connection is provided, the wireless connection is configured to provide an essentially real-time information relay between the ECG electrode and the defibrillator. Thus, a low latency wireless connection is established between the ECG electrodes and the defibrillator. Exemplary low latency wireless connections can be based on an IEEE 802.15 standard, such as the ZigBee communication protocol (other exemplary low latency protocols include ISA100.11a, WirelessHART, and MiWi specification).

After receiving the ECG signals, a processing device in the defibrillator determines a gating signal based on the rescuer's ECG (204). The gating signal is designed to block out or prohibit the administration of the defibrillation shock during vulnerable periods of the rescuer's heart cycle. Various methods can be used to generate the gating signal and are described in more detail herein.

The defibrillator continuously monitors the patient's ECG waveform to determine if/when defibrillation is an appropriate treatment (206). For example, the defibrillator analyzes the patient's heart rhythms to determine whether a shockable rhythm exists that indicates that a defibrillating shock should be applied to the patient. Upon determining that defibrillation is an appropriate therapy for the patient, the defibrillator times the administration of the defibrillation shock based on the gating signal to avoid the identified vulnerable periods of the rescuer's heart cycle (208).

Figure 3:
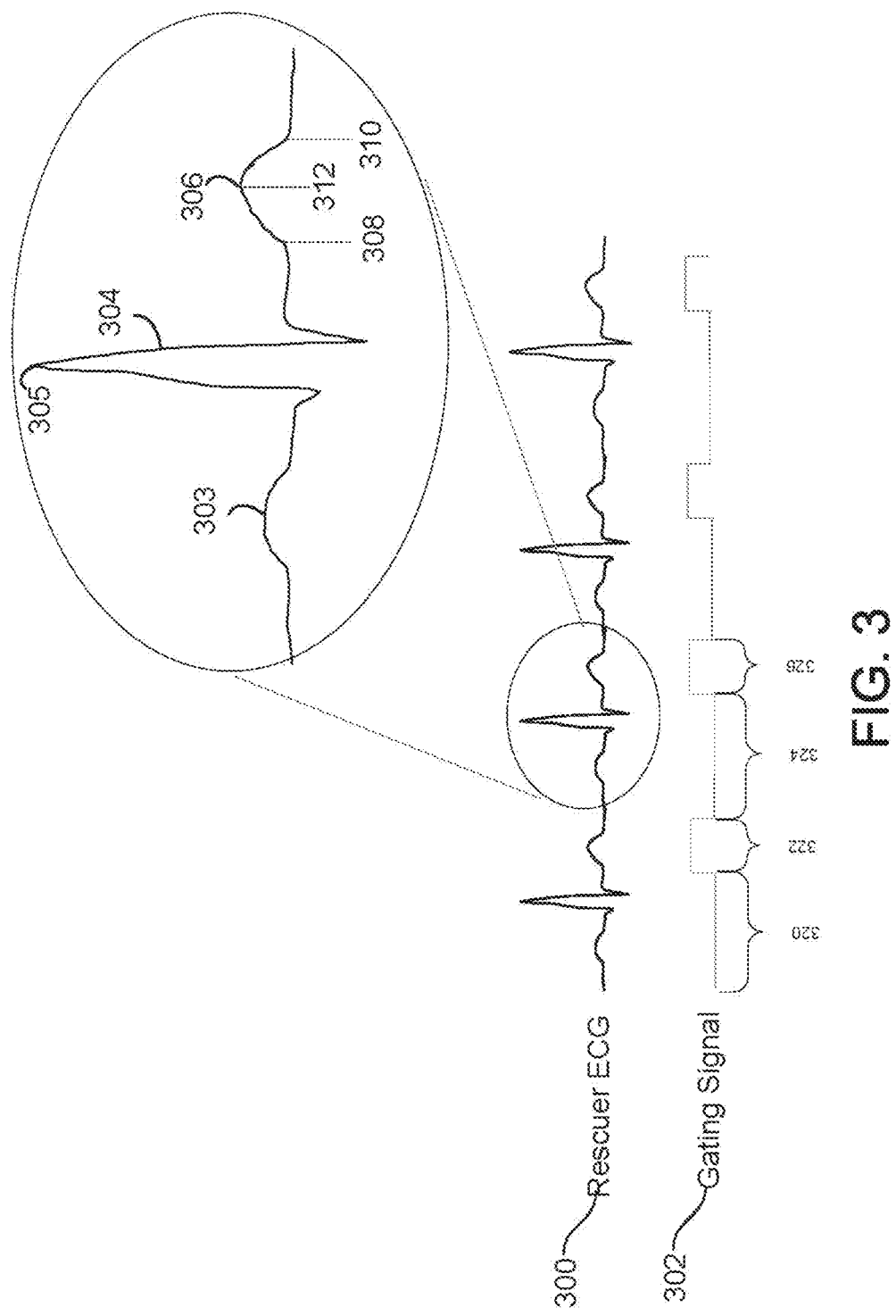
FIG. 3 shows an ECG signal and a gating signal based on the ECG signal.

FIG. 3 shows an example of a monitored ECG signal 300 for a rescuer and a defibrillation gating signal 302 generated based on the ECG signal 300. The ECG signal 300 provides a pattern reflecting the electrical activity of the rescuer's heart. A typical ECG tracing of the cardiac cycle (heartbeat) includes of a P wave 303, a QRS complex 304 (which includes the R wave 305), and a T wave 306. During normal atrial depolarization, the main electrical vector is directed from the sinoatrial node towards the atrioventricular node and spreads from the right atrium to the left atrium. This is visualized as the P wave 303 on the ECG 300. The QRS complex 304 reflects the rapid depolarization of the right and left ventricles. The ventricles have a large muscle mass compared to the atria, so the QRS complex usually has a significantly larger amplitude than the P-wave. The QRS complex 304 includes the R wave 305, which can be seen as the peak in the QRS portion 304 of the ECG signal 300. Due to the large amplitude of the R wave, the R wave is easily identifiable and can be used as a timing mechanism. The T wave 306 represents the repolarization (or recovery) of the ventricles. The interval from the beginning of the QRS complex 304 to the apex of the T wave 306 is referred to as the absolute refractory period and the last half of the T wave 306 is referred to as the relative refractory period (or vulnerable period). In general, the T wave portion of the ECG cycle has a duration of about 140 to 180 ms. Shocks during the vulnerable period of the cardiac cycle (e.g., during the last half of the T wave 306) can induce ventricular fibrillation (VF) if their strength is above the VF threshold (VFT) and less than the upper limit of vulnerability (ULV). The relative timing of the P wave 303, R wave 305 and T wave 306 will remain essentially constant over a short period of time.

The defibrillator determines a gating signal 302 based on the monitored ECG signal 300 for the rescuer. In general, the gating signal provides portions of time during which administration of a defibrillation shock is permitted and portions of time during which administration of the defibrillation shock is prohibited. The prohibited portions of time (e.g., portions 322 and 326) surround the T wave 306 in the monitored rescuer's ECG 300. The timing of the prohibited periods can be based on a delay or offset from the R wave 305. Thus, easier detection of the R wave 305 in the rescuer ECG 300 can be used to time the prohibited periods.

Figure 4:
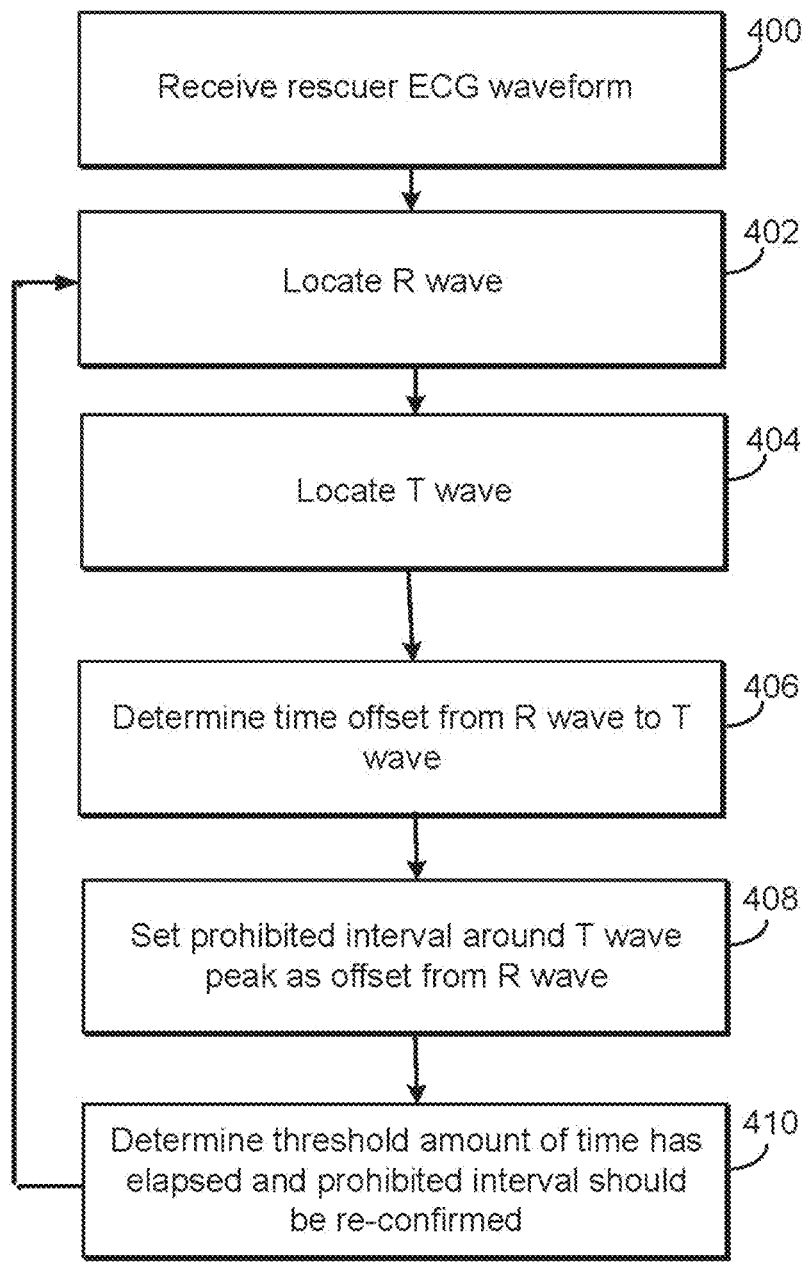
FIG. 4 is a flowchart of a process for generating a gating signal.

FIG. 4 shows an exemplary process for determining the gating signal based on the rescuer's ECG. The defibrillator receives the rescuer's ECG waveform (400) via a wired or low latency wireless communication path (as described above). The defibrillator analyzes the received ECG waveform in order to locate the R wave (402) and the T wave (404). The system determines the R to T wave offset by determining a length of time between the identified peak of the R wave and the identified peak of the T wave. The system then sets a prohibited interval around the T wave peak (408). In one particular example, the prohibited periods are designed to be approximately 50 to 100 ms on each side of a T wave peak. In another example, the prohibited periods have a duration about equal to (e.g., within 10%) the length of time between the R wave and the T wave and centered about the peak of the T wave. In yet another example, the prohibited interval includes the interval from 20% of the peak T wave voltage on the rising edge of the T wave to 20% of the peak T wave voltage on the falling edge of the T wave. In yet another example, the prohibited interval includes the entire duration of the T wave. In yet another example, the prohibited interval includes the relative refractory period. The timing of the prohibited time period is stored as an offset from the R wave peak. Thus, the system stores start and end points of the prohibited period as timing offset from the R wave peak.

While the duration of time between the R wave and the T wave generally remains constant, the duration between the R wave and the T wave may change over time during the rescue due to stress and fatigue of the rescuer. As such, the system determines when the threshold amount of time (e.g., 10 seconds) has elapsed such that the prohibited interval should be reconfirmed (410). If the threshold amount of time has elapsed, the system returns to locating the R and T waves (402, 404).

In some additional examples, the system can store the length of time between the R wave peak and the T wave peak. For each ECG cycle, the system can measure the length of time between the R wave and the T wave and determine if the measured length of time between the R wave and T wave peaks for the current ECG cycle differs from the stored length of time used in setting the prohibited period by more than a threshold amount (e.g., more than 10%). If the length of time has changed by an amount greater than the threshold, then the system re-determines a new prohibited interval around the T wave peak and stores the updated prohibited period.

Figure 5A:
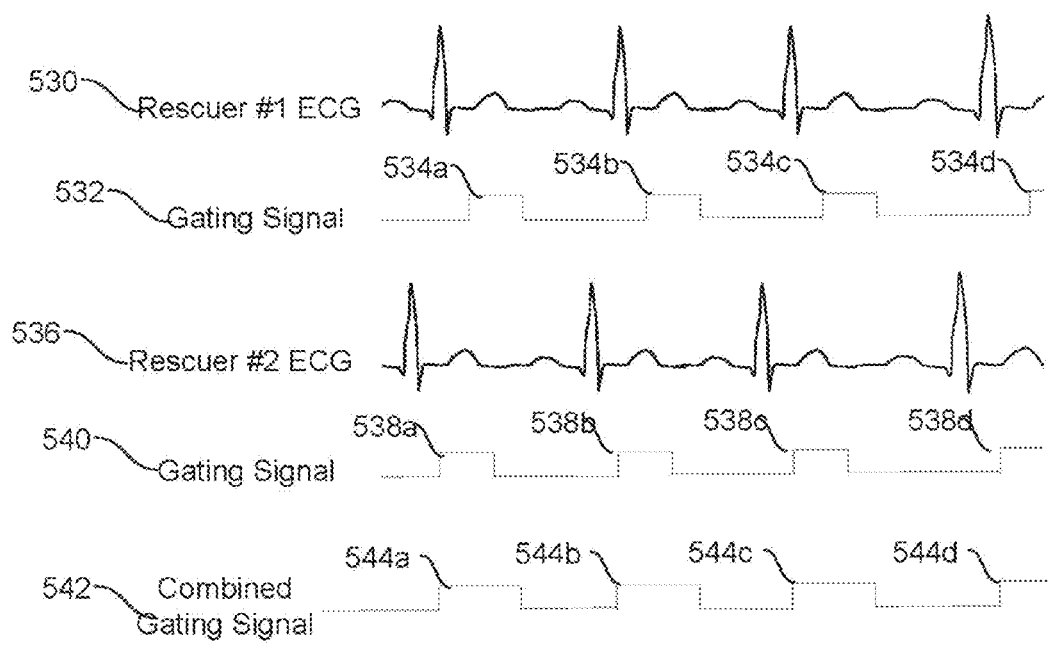
FIG. 5A shows ECG signals from multiple rescuers and a gating signal based on the ECG signals.

In some situations, multiple rescuers work together at the scene of a rescue attempt. In such situations, as shown in FIG. 5A, the defibrillator can receive ECG signals 530, 536 for each of the rescuers participating at the scene of the rescue. In this particular example, two rescuers are cooperating to treat the patient. As such, the defibrillator receives two ECG signals for the rescuers 530, 536. Based on the received ECG signals 530, 536, the defibrillator generates gating signals 532, 540 that include prohibited periods (e.g., periods 534a, 534b, 534c, 534d, 538a, 538b, 538c, and 538d) based on each of the rescuers' heart cycles. In order to ensure that a defibrillation shock is not administered during a vulnerable period of either of the rescuers' heart cycles, the defibrillator combines the two gating signals to generate a combined gating signal 542. The combined gating signal 542 provides a union of the prohibited portions of the two individual gating signals 532 and 540. As such, delivery of the defibrillation shock can be timed to avoid vulnerable periods for multiple rescuers.

While in the examples shown above, an ECG signal of the rescuer was used to gate the administration of a defibrillation shock, other physiologic signals from the rescuer could be used to generate the gating signal. For example, an SpO2 signal or a heartbeat signal could be used.

In some examples a plythysmograph can be placed in contact with the rescuer's skin. In general a plythysmograph measures variations in the size of an organ or body part on the basis of the amount of blood passing through or present in the part. Thus, a signal collected from a plythysmograph can be used to locate the vulnerable portions of a rescuer's heart cycle and generate a gating signal.

In another example, a sensor can be placed in contact with the rescuer that is configured to measure the rescuer's heartbeat signal. Thus, a signal collected from the sensor can be used to locate the vulnerable portions of a rescuer's heart cycle based on the received heartbeat signal and generate a gating signal.

Figure 5B:
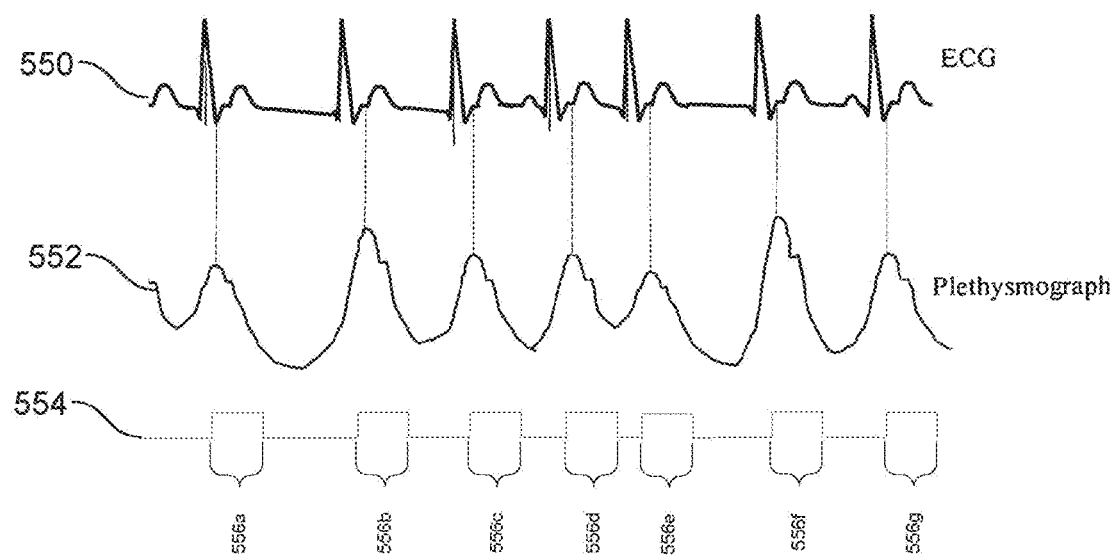
FIG. 5B shows an ECG signal, an SpO2 signal and a gating signal based on the SpO2 signal.

In another example, an SpO2 sensor can be placed in contact with the rescuer's skin for example on the rescuer's earlobe or finger. The SpO2 sensor measures an SpO2 signal for the rescuer. The signal collected from the SpO2 sensor can be used to locate the vulnerable portions of a rescuer's heart cycle based on the received heartbeat signal. More particularly, as shown in FIG. 5B, a monitored SpO2 signal 554 includes a peak that generally follows the QRS complex (e.g., item 304 in FIG. 3) and another peak that generally aligns with T wave portions of an ECG signal 550. As such, the peak of the SpO2 signal can be used to identify the location/timing of the T wave within the SpO2 cycle. Based on the location of the T wave in the SpO2 signal, a gating signal 554 can be generated with periods 556a-g that correspond to prohibited times for administration of the defibrillation signal. The prohibited times can be determined as offset times from the peak of the SpO2 signal. In one example, the prohibited times can correspond to a predetermined length of time beginning from the peak of the SpO2 signal and continuing for a predetermined period of time (e.g., 100 ms). In another example, the prohibited period can include the period of time between the main peak of the SpO2 signal and the main valley of the SpO2 signal.

In some examples, it is believed that using the SpO2 signal to generate the defibrillation gating signal can provide advantages relating to the ease of use by the rescuer. Unlike an ECG lead which must be placed in contact with the skin under the rescuer's clothing. The SpO2 sensor can simply be affixed to the rescuer's ear.

Figure 6:
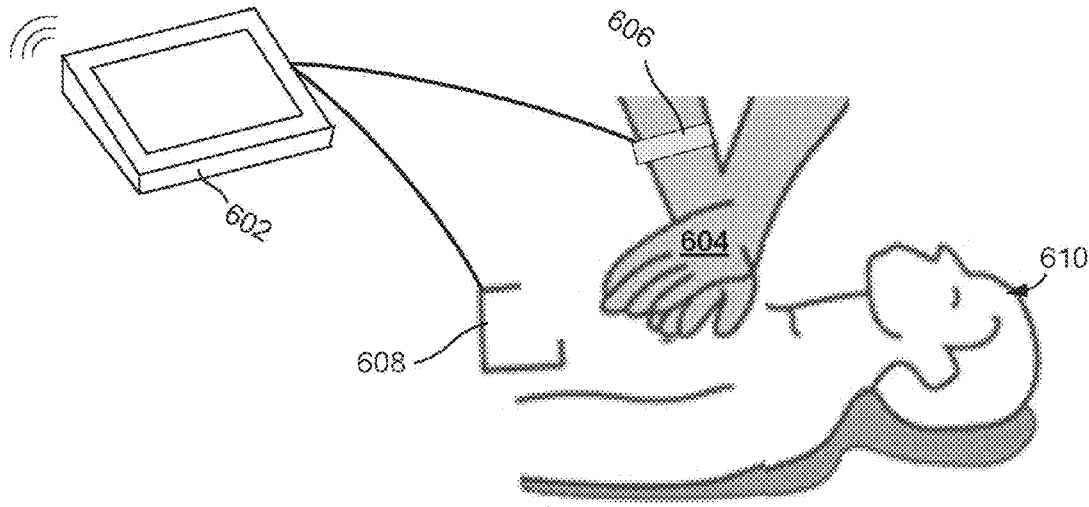
FIG. 6 is an overhead view of rescuers performing CPR on a patient.

In some additional examples, the defibrillator can include safety mechanisms for disabling the administration of a defibrillation pulse based on electrical contact between the rescuer and the patient. For example, as shown in FIG. 6, a rescuer 604 can provide CPR or a different treatment to a patient 610. In doing so, there are times during which the rescuer is in contact with the patient 610. If a defibrillation shock was administered while electrical contact existed between the rescuer 604 and the patient 610, the rescuer could suffer from the shock. In order to prevent the rescuer 604 from receiving the electrical shock provided to the patient 610, the defibrillator is configured to monitor contact between the rescuer 604 and the patient 610. In this example, the rescuer wears a monitor 606 that is in electrical contact with his/her skin. The defibrillator 602 provides a small electrical current or signal to the defibrillation pads 608 attached to the patient 610. If electrical contact exists between the patient 610 and the rescuer 606, this current/voltage will be observable at the monitor device 606. If the defibrillator 602 receives a signal from monitor 606 indicative of electrical contact between the patient 610 and the rescuer 604, the defibrillator 602 disables administration of the defibrillation shock. The defibrillator can also instruct the rescuer to stand clear or remove his/her hands from the patient when contact is observed and administration of a defibrillation shock is advisable treatment for the patient (e.g., as shown in item 134 of FIG. 1).

Figure 7:
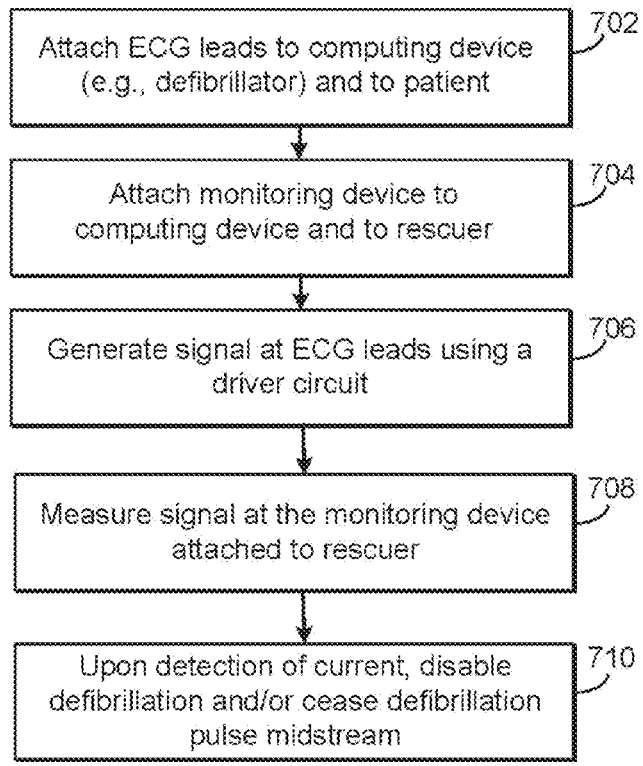
FIG. 7 is a flow chart of a process for prohibiting defibrillation upon detection of (skin on skin) contact between the rescuer and patient.

FIG. 7 shows a flowchart of a process for disabling administration of a defibrillation pulse based on contact between a rescuer and a patient. The process includes attaching ECG leads to a computing device, such as a defibrillator and to the patient (702). The process also includes attaching a monitoring device to the computing device and to the rescuer (704). Exemplary monitoring devices can include a conductive pad placed in contact with the rescuer's skin and one or more circuits for measuring a resistance and/or a capacitance observed in a circuit. Such monitoring devices can be included in a wrist or ankle strap secured to the rescuer. After attaching both the monitoring device and the ECG leads to the rescuer and patient respectively, the defibrillator generates a signal at the ECG leads using a driver circuit (706). The signal can be a low level current that is applied continuously or at predetermined intervals to the ECG pads on the patient. The defibrillator also measures a signal at the monitoring device attached to the rescuer (708). As described in more detail below, this signal will differ depending on whether the rescuer is in electrical contact with the patient. By continuously monitoring whether a signal indicative of contact is observed at the monitoring device, the system can quickly cease administration of a defibrillation pulse if contact is observed. Thus, upon detection of the applied signal from the ECG pads at the monitoring device, the defibrillator can disable administration of the defibrillation shock and/or cease administration of the defibrillation pulse midstream if the defibrillation device has already initiated the defibrillation pulse (710). For example, the defibrillation pulse can be stopped within 5-15 μs (e.g., within 10 μs) of observing contact.

In one particular example, defibrillation pulse includes a positive phase and a negative phase with an instantaneous stoppage there between. After the positive phase, the defibrillation pulse is stopped completely and then the polarity is flipped for the negative phase. The same circuitry that is used to stop the defibrillation pulse between the positive and negative phases can be used to nearly instantaneously stop the pulse at any point during delivery of the defibrillation pulse.

Figure 8A:
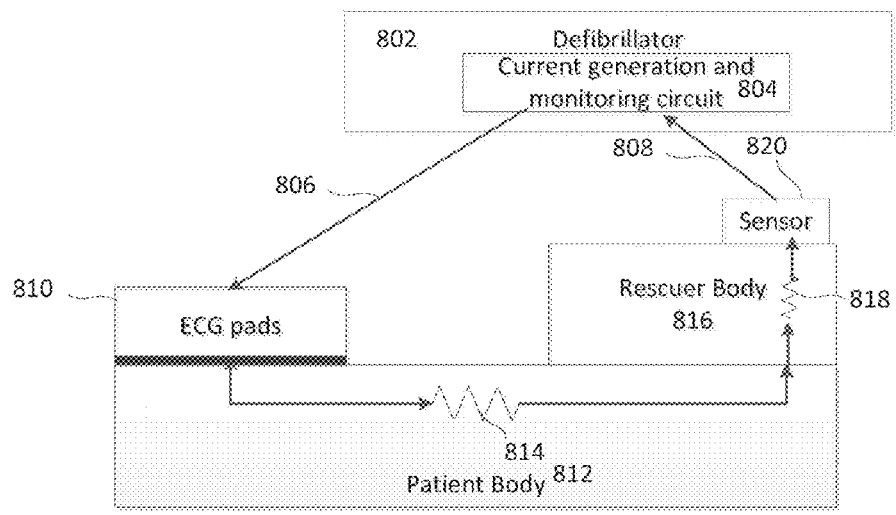
FIGS. 8A and 8B are exemplary diagrams of devices for the detection of contact between the rescuer and patient.
Figure 8B:
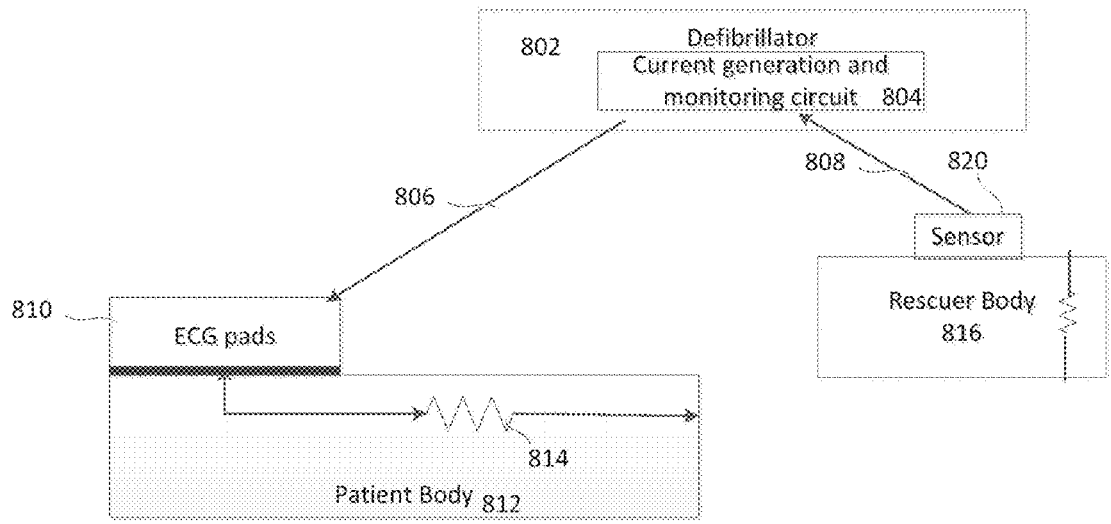

FIGS. 8A and 8B provide examples of the monitoring of contact between a patient's body 812 and a rescuer's body 816. As shown in FIG. 8A, the defibrillator 802 includes a current generation and monitoring circuit 804. The current generation and monitoring circuit 804 generates a signal that is sent to one or more ECG pads 810 over a wire 806. The ECG pads 810 are in contact with the patient's body 812, such that the signal is transmitted from the current generation and monitoring circuit 804 and into the patient's body 812. The patient's body serves as a conductive medium over which the signal can be propagated (e.g., along path 814). If the rescuer's body 816 is in contact with the patient's body 812, then the conductive path continues from path 814 through the rescuer's body 816 along path 818. A sensor 820 is in contact with the rescuer's skin and is connected to the current generation and monitoring circuit 804. Thus, if the rescuer's body and patient's body are in electrical contact, a current loop is completed and the signal sent from the current generation and monitoring circuit 804 flows across line 806, through the ECG pads 810, across the patient's body 814, through the rescuer's body 816, into the sensor 820 and back to the current generation and monitoring circuit 804. In contrast, (as shown in FIG. 8B) this current path does not exist when the patient's body 812 is not in electrical contact with the rescuer's body 816. In such a situation the signal generated by the current generation and monitoring circuit 804 is not received or sensed by sensor 820 attached to the rescuers body 816. As such, by monitoring the current present at device 820, it can be determined whether the rescuer's body is in contact with the patient's body.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

The term "machine-readable signal" refers to any signal used to provide machine instructions and/or data to a programmable processor.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

Many other implementations other than those described may be employed, and may be encompassed by the following claims.

What is claimed is:

1. A medical system, comprising:
a device configured to be placed in contact with the skin of a rescuer;
an ECG lead configured to be placed in contact with the skin of a patient; and
a safety mechanism configured to:
detect electrical contact between the patient and the rescuer by applying a signal to the ECG lead and measuring a signal responsive to the applied signal at the device in contact with the skin of the rescuer; and
prohibit delivery of a defibrillation shock upon detection of electrical contact between the rescuer and the patient,
wherein measuring the signal responsive to the applied signal comprises measuring a signal transmitted between the ECG lead and the device in contact with the skin of the rescuer using the patient's body and the rescuer's body as conductive mediums.

2. The system of claim 1, wherein the safety mechanism is further configured to enable delivery of the defibrillating shock to the patient upon detection of an absence of contact between the patient and the rescuer.

3. The system of claim 1, wherein the device configured to be placed in contact with the skin of the rescuer comprises a wrist strap.

4. The system of claim 1, further comprising a notification device configured to provide instructions for removing the electrical contact between the patient and the rescuer.

5. The system of claim 1, wherein the device in contact with the skin of the rescuer comprises a wrist or ankle strap.

6. The system of claim 1, wherein the safety mechanism comprises a driver circuit configured to generate the signal for applying to the ECG lead.

7. The system of claim 1, wherein the signal for the ECG lead is applied in a substantially continuous manner.

8. The system of claim 1, wherein the signal for the ECG lead is applied at predetermined intervals.

9. The system of claim 1, wherein the device comprises a conductive pad.

10. The system of claim 9, wherein the electrical contact is detected by measuring at least one of a resistance and a capacitance.

11. The system of claim 1, wherein the safety mechanism comprises circuitry configured to stop a defibrillation pulse between a positive phase and a negative phase of the defibrillation pulse.

12. The system of claim 1, wherein the safety mechanism prohibits delivery of the defibrillation shock by disabling administration of a defibrillation pulse upon detection of the electrical contact between the rescuer and the patient.

13. The system of claim 1, wherein the safety mechanism prohibits delivery of the defibrillation shock by stopping an initiated defibrillation pulse upon detection of the electrical contact between the rescuer and the patient.

14. The system of claim 13, wherein the initiated defibrillation pulse is stopped within 5-15 μs of detection of the electrical contact between the rescuer and the patient.

15. The system of claim 13, wherein the initiated defibrillation pulse is stopped within 10 μs of detection of the electrical contact between the rescuer and the patient.

16. The system of claim 1, wherein the applied signal is an electrical current of magnitude lower than the magnitude of a defibrillation current.

17. A method comprising:
applying a signal to an ECG lead in contact with the skin of a patient;
measuring a signal at a device in contact with the skin of a rescuer, the signal being responsive to the applied signal;
detecting electrical contact between the patient and the rescuer based on the detected signal; and
prohibiting delivery of a defibrillation shock upon detection of electrical contact between the rescuer and the patient,
wherein measuring the signal responsive to the applied signal comprises measuring a signal transmitted between the ECG lead and the device in contact with the skin of the rescuer using the patient's body and the rescuer's body as conductive mediums.

18. The method of claim 17, further comprising enabling delivery of the defibrillating shock to the patient upon detection of an absence of contact between the patient and the rescuer.

19. The method of claim 17, further comprising providing, by a notification device, instructions for removing the electrical contact between the patient and the rescuer.

20. The method of claim 17, wherein the signal for the ECG lead is applied in a substantially continuous manner.

21. The method of claim 17, wherein the signal for the ECG lead is applied at predetermined intervals.

22. The method of claim 17, wherein prohibiting the delivery of the defibrillation shock comprises disabling administration of a defibrillation pulse upon detection of the electrical contact between the rescuer and the patient.

23. The method of claim 17, wherein prohibiting the delivery of the defibrillation shock comprises stopping an initiated defibrillation pulse upon detection of the electrical contact between the rescuer and the patient.

24. The method of claim 23, wherein the initiated defibrillation pulse is stopped within 5-15 μs of detection of the electrical contact between the rescuer and the patient.

25. The method of claim 23, wherein the initiated defibrillation pulse is stopped within 10 μs of detection of the electrical contact between the rescuer and the patient.

26. The method of claim 17, wherein detecting the electrical contact comprises measuring at least one of a resistance and a capacitance.

27. The method of claim 17, wherein the applied signal is an electrical current of magnitude lower than the magnitude of a defibrillation current.

28. One or more machine-readable storage devices having encoded thereon machine readable instructions for causing one or more processors to perform operations comprising:
applying a signal to an ECG lead in contact with the skin of a patient;
measuring a signal at a device in contact with the skin of a rescuer, the signal being responsive to the applied signal;
detecting electrical contact between the patient and the rescuer based on the detected signal; and prohibiting delivery of a defibrillation shock upon detection of electrical contact between the rescuer and the patient wherein measuring the signal responsive to the applied signal comprises measuring a signal transmitted between the ECG lead and the device in contact with the skin of the rescuer using the patient's body and the rescuer's body as conductive mediums.

29. The one or more machine-readable storage devices of claim 28, further comprising machine-readable instructions for providing, on a notification device, instructions for removing the electrical contact between the patient and the rescuer.

30. The one or more machine-readable storage devices of claim 28, wherein the signal for the ECG lead is applied in a substantially continuous manner.

31. The one or more machine-readable storage devices of claim 28, wherein the signal for the ECG lead is applied at predetermined intervals.

32. The one or more machine-readable storage devices of claim 28, wherein prohibiting the delivery of the defibrillation shock comprises disabling administration of a defibrillation pulse upon detection of the electrical contact between the rescuer and the patient.

33. The one or more machine-readable storage devices of claim 28, wherein prohibiting the delivery of the defibrillation shock comprises stopping an initiated defibrillation pulse upon detection of the electrical contact between the rescuer and the patient.

34. The one or more machine-readable storage devices of claim 33, wherein the initiated defibrillation pulse is stopped within 5-15 μs of detection of the electrical contact between the rescuer and the patient.

35. The one or more machine-readable storage devices of claim 33, wherein the initiated defibrillation pulse is stopped within 10 μs of detection of the electrical contact between the rescuer and the patient.

36. The one or more machine-readable storage devices of claim 28, wherein detecting the electrical contact comprises measuring at least one of a resistance and a capacitance.

37. The one or more machine-readable storage devices of claim 28, wherein the applied signal is an electrical current of magnitude lower than the magnitude of a defibrillation current.

* * * * *